United States Patent
Charles (10) Patent No.: US 11,033,186 B2
(45) Date of Patent: Jun. 15, 2021

(54) METHODS AND SYSTEM FOR IMAGING AN INNER LIMITING MEMBRANE USING A STAIN

(71) Applicant: NOVARTIS AG, Basel (CH)

(72) Inventor: Steven T. Charles, Memphis, TN (US)

(73) Assignee: Alcon Inc.

(*) Notice: Subject to any disclaimer, the term of this patent is extended or adjusted under 35 U.S.C. 154(b) by 23 days.

(21) Appl. No.: 15/054,287

(22) Filed: Feb. 26, 2016

(65) Prior Publication Data

US 2017/0245754 A1 Aug. 31, 2017

(51) Int. Cl.
| A61B 3/14 | (2006.01) |
| A61B 3/10 | (2006.01) |
| A61B 3/00 | (2006.01) |
| A61B 3/12 | (2006.01) |
| A61B 3/13 | (2006.01) |

(52) U.S. Cl.
CPC ............ *A61B 3/102* (2013.01); *A61B 3/005* (2013.01); *A61B 3/0025* (2013.01); *A61B 3/0058* (2013.01); *A61B 3/1225* (2013.01); *A61B 3/13* (2013.01); *A61B 3/14* (2013.01)

(58) Field of Classification Search
CPC ..... A61B 3/102; A61B 5/0059; A61B 5/0066; A61B 3/0025; A61B 3/005; A61B 3/0058; A61B 3/1225; A61B 3/13; A61B 3/14; A61K 49/001; A61K 49/006
USPC ........................................................ 351/206
See application file for complete search history.

(56) References Cited

U.S. PATENT DOCUMENTS

| 2008/0084538 A1* | 4/2008 | Maeda ................ A61B 3/1241 351/206 |
| 2008/0206149 A1* | 8/2008 | Haritoglou ......... A61K 49/0021 424/9.6 |
| 2009/0021746 A1* | 1/2009 | Toida ................... A61B 5/0066 356/484 |
| 2011/0043661 A1* | 2/2011 | Podoleanu ............. A61B 3/102 348/239 |
| 2012/0019777 A1 | 1/2012 | Hauger |
| 2012/0026462 A1 | 2/2012 | Uhlhorn |
| 2012/0033227 A1* | 2/2012 | Bower ................... A61B 3/102 356/479 |
| 2013/0208245 A1* | 8/2013 | Campbell ............ A61B 3/0025 351/246 |
| 2013/0258284 A1* | 10/2013 | Makihira ................ A61B 3/14 351/206 |

(Continued)

FOREIGN PATENT DOCUMENTS

WO 2010060622 A2 6/2010

*Primary Examiner* — Mahidere S Sahle (57) ABSTRACT

Systems and methods for imaging tissue are described. Particularly, systems and methods of imaging an inner limiting membrane, epi-retinal membrane, or posterior vitreous cortex of a patient's eye are disclosed. Imaging an inner limiting membrane, epi-retinal membrane, or posterior vitreous cortex may include applying a stain to the inner limiting membrane, epi-retinal membrane, or posterior vitreous cortex of the patient's eye, causing the stain to produce fluorescent light having a wavelength within a near-infrared range, capturing the fluorescent light, and producing an Optical Coherence Tomography (OCT) image of the inner limiting membrane, epi-retinal membrane, or posterior vitreous cortex with an OCT imaging system that is configured to detect light within the near-infrared range.

12 Claims, 4 Drawing Sheets

(56) References Cited

U.S. PATENT DOCUMENTS

2014/0307078 A1 10/2014 Charles
2016/0029892 A1 2/2016 Charles
2017/0164826 A1* 6/2017 Buckland ............... A61B 3/102

* cited by examiner

METHODS AND SYSTEM FOR IMAGING AN INNER LIMITING MEMBRANE USING A STAIN

TECHNICAL FIELD

The present disclosure is directed to methods and systems for ophthalmic medical procedures, and more particularly, to methods and systems involving imaging for such procedures.

BACKGROUND

Many microsurgical procedures require precision cutting and/or removal of various body tissues. For example, Internal Limiting Membrane (ILM) removal; epi-retinal membrane (ERM) removal; and posterior vitreous cortex (PVC) removal are useful surgical treatments of different macular surface diseases. However, the surgical techniques for ILM and ERM peeling and PVC removal require skill and patience. Precise and carefully constructed surgical instruments are used for each segment of the surgical technique.

ILM, ERM, and PVC procedures use a two-step technique. The first step includes gaining an edge of the membrane and the second step includes grasping and peeling the membrane. Some operators use a scraper to gain the edge of the membrane. The operator gently scrapes the membrane to separate membrane edges so that an edge is ready to be grasped. Next, the operator introduces a special forceps to grasp and peel the membrane. However, since each step requires patience and precision, an operator may sometimes scrape and then attempt to grasp the tissue multiple times during a single surgical procedure. Another method of removing these tissues involves using end-grasping forceps to grasp the tissue without locating an edge and pinch peeling the tissue.

To aid the operator with these types and other types of surgical procedures, operators may use an imaging system that presents a microscope view of the tissue to be treated, such as tissue of the patient's eye. Accordingly, the user of such an imaging system may be provided with a close-up view of the surgical instruments, such as forceps or other tools, as well as the region of the eye that is of interest. In some cases, the operator may also be provided with an Optical Coherence Tomography (OCT) image of the region of the eye that is of interest. OCT imaging generally utilizes near-infrared light and is able to obtain or generate images of tissue beneath the surface. The ILM itself is a thin transparent piece of tissue that is generally not resolvable through microscope and OCT imaging techniques.

SUMMARY

According to some implementations, a method for imaging an inner limiting membrane of an eye includes applying a stain to the inner limiting membrane of the eye, causing the stain to produce fluorescent light having a wavelength within a near-infrared range, and capturing the fluorescent light and producing an Optical Coherence Tomography (OCT) image of the inner limiting membrane with an OCT imaging system that is configured to detect light within the near-infrared range.

A method includes applying a stain to an inner limiting membrane of an eye, causing the stain to produce fluorescent light having a wavelength within a range outside a visible spectrum, and capturing a microscope image of the inner limiting membrane with a microscope imaging system that is sensitive to light within the range outside the visible spectrum.

A method includes applying a stain to an inner limiting membrane of an eye, directing light from an excitation light source at the stain to cause the stain to produce fluorescent light having a wavelength within a near-infrared range, capturing the fluorescent light and generating an Optical Coherence Tomography (OCT) image of the inner limiting membrane with an OCT imaging system, the OCT imaging system configured to detect light within the near-infrared range, and while capturing the fluorescent light and generating the OCT image, capturing a microscope image of the inner limiting membrane with a microscope imaging system that is sensitive to light within the near-infrared range.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure is directed to methods and systems for imaging an ILM with both OCT and microscope imaging systems during a surgical procedure. For example, a user may observe a region of interest, such as eye tissue of a patient, using an imaging system that includes both a microscope imaging system and an OCT imaging system. Such an imaging system may permit a user to observe both a conventional microscope image and an OCT image while performing an ophthalmic surgical procedure such as an ILM removal. A conventional microscope image may be typically observed using light that is within the visible spectrum having a wavelength ranging between about 400 nanometers and 700 nanometers. An OCT image may be generated using light in the near-infrared range having a wavelength within a range of about 700 nanometers to 1700 nanometers. Some implementations may permit a user to obtain OCT images using light in the visible spectrum range. Thus, an OCT image may be obtained using light within any practicable wavelength range. In some cases, the OCT image may provide a cross-sectional view of tissue in the region of interest within the eye and may be used to visualize tissue below the outer surface tissue. The ILM itself is a thin, transparent tissue having a thickness of approximately three micrometers. Because of this, the ILM may be difficult to resolve using an OCT imaging system.

Although removal of the ILM is discussed in the various examples presented herein, the scope of the disclosure is not so limited. Rather, one or more of the various examples may be used to remove the ERM or PVC. The ERM and vitreous, such as the PVC, are typically thicker, less transparent, and less amorphous than the ILM, making the ERM and vitreous, particularly the PVC, more visible than the ILM through both a microscope and with OCT imaging. Therefore, the following discussion is made with respect to the ILM due to the difficulty associated with the ILM's detection compared to other tissues. However, the scope of the disclosure is intended to encompass other tissues, such as the ERM and PVC.

Conventional implementations for visualizing the ILM with standard microscope imaging systems may employ various dyes to stain the ILM ERM, or vitreous, such as the PVC. The practice of using a dye to stain the ILM, ERM, or vitreous, including the PVC, is referred to as chromovitrectomy. Current chromovitrectomy practices, however, do not allow the ILM to be viewed through OCT imaging techniques.

According to principles described herein, to make the ILM resolvable through OCT imaging techniques, the ILM may be stained with a dye that is selected to fluoresce within the near-infrared range. Directing light from an excitation light source at the stained ILM may cause the stained ILM to emit fluorescent light having a wavelength within the near-infrared range. The emitted light in the near-infrared range may be resolved by an OCT imaging system. As such, a user may be able to better utilize OCT images of the ILM during an ophthalmic procedure. Better OCT images may enable the user to better perform the desired treatment procedures, potentially resulting in a better patient outcome. In some example implementations, a microscope imaging system uses sensors that are sensitive to light within the near-infrared range. Thus, the microscope imaging system may also resolve the stained ILM for better microscope imaging.

Figure 1:
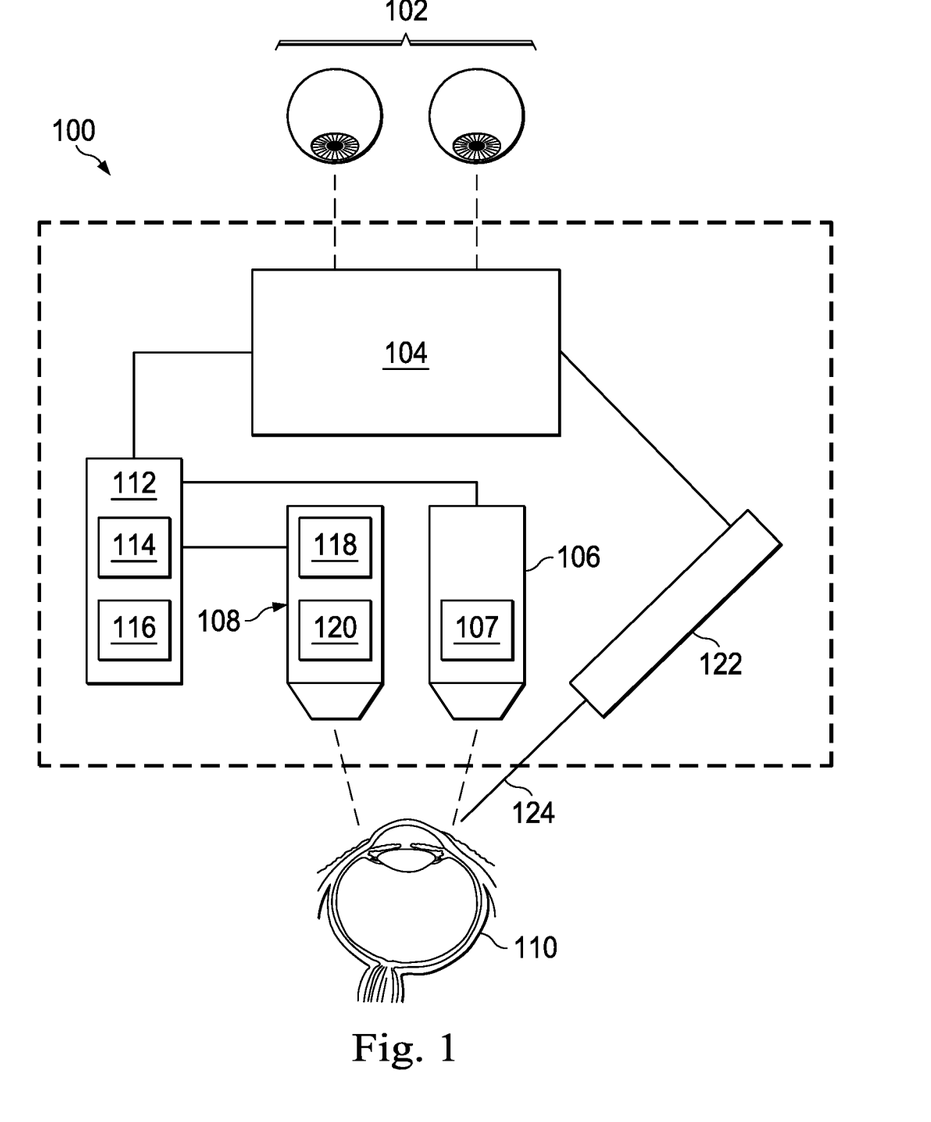
FIG. 1 is a block diagram showing an illustrative ophthalmic surgical system.

FIG. 1 shows an illustrative ophthalmic imaging system 100. According to the example embodiment in FIG. 1, the ophthalmic imaging system 100 includes an image viewer 104, a microscope imaging system 106, an OCT imaging system 108, an excitation light source 122, and a control system 112. The ophthalmic imaging system 100 may be arranged to provide a user 102 with one or both of a microscope view or image and an OCT image of the region of interest within a target region of the patient's body. In the example implementation presented in FIG. 1, the target region is represented by an eye 110 of the patient.

The microscope imaging system 106 may obtain images of the patient's eye 110 using light within the near-infrared spectrum as well as the visible spectrum. The near-infrared spectrum defines a wavelength range of light that is typically not visible to the human eye. As indicated above, the near-infrared spectrum may include electromagnetic radiation having a wavelength generally within a range of 700 nanometers to 1700 nanometers. The visible spectrum defines the wavelength range of light that is visible to the human eye. The visible spectrum includes electromagnetic radiation having a wavelength that is, as indicated above, generally within a range of about 400 nanometers to 700 nanometers, though this wavelength range may vary slightly for different individuals. The microscope imaging system 106 may use a system of lenses to provide a magnified view of the patient's eye 110 or even a specific region of interest within the patient's eye 110.

The microscope imaging system 106 may include one or more sensors 107 that are sensitive to light having a wavelength within the near-infrared range in order to obtain images of the stained ILM. In some implementations, the sensors 107 may be Charge-Coupled Device (CCD) sensors that sense light having a wavelength within the near-infrared range. In other implementations, the sensors 107 may be Complementary Metal-Oxide-Semiconductor (CMOS) sensors that sense light having a wavelength within the near-infrared range. In yet other implementations, the sensors 107 may include both CCD and CMOS sensors. Some implementations may include other sensors 107 arranged to detect light having a wavelength within the near-infrared range. The sensors 107 of the microscope imaging system 106 provide captured images to the control system 112, which then processes the captured images. The processed images may then be provided to the image viewer 104, which are then displayed to the user 102.

The OCT imaging system 108 obtains OCT images of the patient's eye 110. It uses various techniques to obtain depth resolved images of the patient's tissue beneath the surface of the tissue that are not able to be obtained from the use of a standard microscope, including the microscope imaging system 106. This is done using coherence gating based on light that is within the OCT spectrum. The OCT spectrum corresponds to the near-infrared spectrum. As indicated above, this range includes electromagnetic radiation having a wavelength between about 700 nanometers and 1700 nanometers. By using coherence gating, the OCT imaging system 108 may display an image of tissue below the surface tissue and generate a cross-sectional view of such tissue. As such, the OCT imaging system 108 may be used to obtain a cross-sectional view of the region of interest being treated by the user 102. As such, the OCT image may allow the user 102 to see how interactions between the surgical instrument and the surface of an ILM affect the tissue below the surface of the ILM. This may help provide better patient outcomes. For example, the user 102 may use the cross-sectional image to help avoid accidental damage to the underlying retina. The user 102 may also use the cross-sectional image to identify and smooth ILM wrinkles. The user 102 may obtain additional alternative advantages. In some implementations, the OCT imaging system 108 is integrated with the conventional microscope imaging system 106 in a manner such as that shown in the example implementation of FIG. 1. In other implementations however, the OCT imaging system 108 may be a separate apparatus that provides the OCT images to the image viewer 104 or other imaging device.

The OCT imaging system 108 includes various components that are used to perform the OCT imaging function. For example, the OCT imaging system 108 may include an OCT light source 118 that emits an OCT beam of light at a region of interest at the surgical site, such as a portion of the patient's eye 110. The emitted OCT beam of light may be light within the near-infrared spectrum. The OCT imaging system 108 may also include an OCT capture device 120 that detects OCT light reflected from the region of interest. The OCT imaging system 108 may then use the information obtained by the OCT capture device 120 to construct an image of the region of interest. This in turn may be visibly displayed to the user 102 as described below. In some examples, the constructed image may be a two-dimensional cross-section of the region of interest. In such examples, the constructed image may provide a view beneath the surface of tissue within the region of interest. In other examples, the constructed image may be a three-dimensional image that provides a three-dimensional view beneath the surface of the tissue within the region of interest.

The image viewer 104 may display to the user 102 or other operator the images obtained by one or both of the microscope imaging system 106 and the OCT imaging system 108. In some implementations, the images are simultaneously displayed. In other implementations, the images may be displayed one at time. The user 102 may toggle between the images, or the images may be set to switch between images with or without user input.

The image viewer 104 may display the images in a variety of ways. For example, in some implementations, the image viewer 104 is a heads-up display, such as a monitor that can be viewed by multiple users simultaneously. In other implementations, the image viewer 104 is a microscope eyepiece. Still other image viewers are contemplated. In some examples, the microscope imaging system 106 may provide stereoscopic images formed of at least two images. In such examples, the image viewer 104 may display the at least two images to different eyes of the user 102, thus creating a three dimensional effect.

The control system 112 is a computing system that may process images obtained from the OCT imaging system 108 and the microscope imaging system 106. In some cases, the OCT imaging system 108 and the microscope imaging system 106 may capture images of a region of interest simultaneously. The control system 112 may process images received by the microscope imaging system 106 to make the images viewable by the human eye. Specifically, the control system 112 may adjust images captured using light within the near-infrared range to correspond to a wavelength range within the visible spectrum so as to be viewable by a human user 102. Similarly, the control system 112 may process the image data from the OCT imaging system 108 to provide a human viewable OCT image. The control system 112 may then provide the processed images to the image viewer 104 for display to the user 102. In some implementations, the control system 112 may be physically integrated with the OCT imaging system 108, the microscope imaging system 106, or both. In some implementations, the control system 112 may be physically integrated with the image viewer 104. In still other implementations, the control system 112 is a discrete component that is separate from, and in communication with, the image viewer 104, the microscope imaging system 106, and the OCT imaging system 108.

The control system 112 may include a processor 114 and a memory 116. The memory 116 may include various types of memory including volatile memory (such as Random Access Memory (RAM)) and non-volatile memory (such as solid state storage). The memory 116 may store computer readable instructions, that when executed by the processor 114, cause the control system 112 to perform various functions, including the image capture and processing functions described herein. The memory 116 may also store data representing images captured by the OCT imaging system 108 and the microscope imaging system 106 as well as processed versions of those images.

The excitation light source 122 emits excitation light 124 that causes the stain on the tissue, such as on the ILM, to fluoresce within the near-infrared range. The wavelength of the excitation light 124 may be selected according to the type of dye that is used to stain the ILM. For example, different types of dyes may fluoresce within the near-infrared range in response to excitation light 124 of different wavelengths. The excitation light 124 may have a wavelength within a different range than the wavelength of the fluorescent light being emitted by the stain. For example, the excitation light source 122 may produce excitation light 124 within an ultraviolent range (e.g. 100-400 nanometers) or excitation light 124 within the visible spectrum. When the excitation light 124 reaches the stain, it excites the stain and causes the stain to produce light within the near-infrared range (e.g. 700-1700 nanometers). While these ranges are given as examples, it is worth noting that other light ranges and wavelengths may be used.

In the present example, the excitation light source 122 is illustrated as a discrete element that is separate from the OCT imaging system 108 and the microscope imaging system 106. In some implementations, the light source 122 may be a hand-held instrument. All or a portion of the light source 122 may be introduced to the globe of the eye through a cannula so that the light is introduced within the eye. In other instances, the light source 122 may be disposed outside the eye, and light produced by the light source 122 may be directed into the eye. In some examples, the excitation light source 122 may be integrated within the OCT imaging system 108 or the microscope imaging system 106. In some implementations, the OCT light source 118 may produce, alone or in addition to excitation light from the light source 122, the excitation light 124 to cause the stain on the ILM to fluoresce within the near-infrared spectrum.

Figure 2:
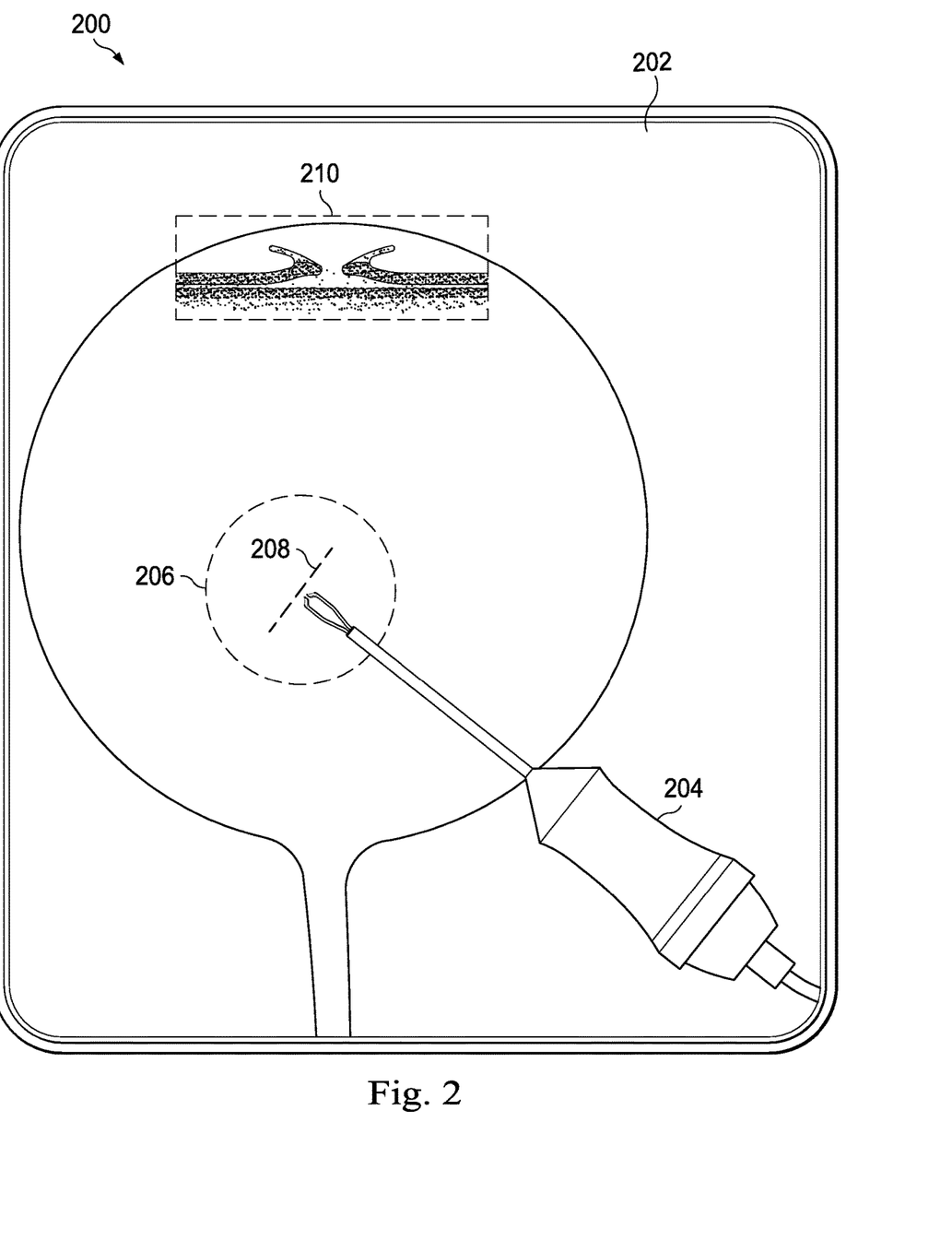
FIG. 2 is shows an illustrative image of a portion of a patient's eye as may be seen through an OCT-enabled microscope during a surgical procedure.

FIG. 2 is a diagram showing an illustrative combined microscope and OCT view 200 of a patient's eye as presented or displayed by an image viewer (e.g., image viewer 104, as shown in FIG. 1). According to the present example, the image viewer shows an OCT image 210 overlaid over a microscope image 202 and displays the images 210, 202 to the user (e.g., user 102, shown in FIG. 1). Thus, the user can view a potential region of interest 206, along with the surgical instrument 204 being used to operate within or treat the region of interest 206. The dotted line 208 in FIG. 2 represents the cross-sectional line at which the cross-sectional OCT image 210 is taken. Thus, as may be seen, image viewer projects the OCT image 210 onto the microscope image 202 in a manner permitting the user to visually observe both images 202, 210 at once.

The microscope image 202 may represent tissue captured by or viewable through the microscope imaging system (e.g., microscope imaging system 106, as shown in FIG. 1) using light within the visible spectrum and/or light within the near-infrared spectrum. The microscope imaging system may be configured to sense light within the visible spectrum as well as light within the near-infrared spectrum. Because light within the near-infrared spectrum is not viewable to the human eye, a control system (e.g., control system 112, shown in FIG. 1) can be used to convert image data obtained with the near-infrared sensors (e.g., sensors 107, also shown in FIG. 1) into image data in the form of an image that is viewable to a human.

Figure 3A:
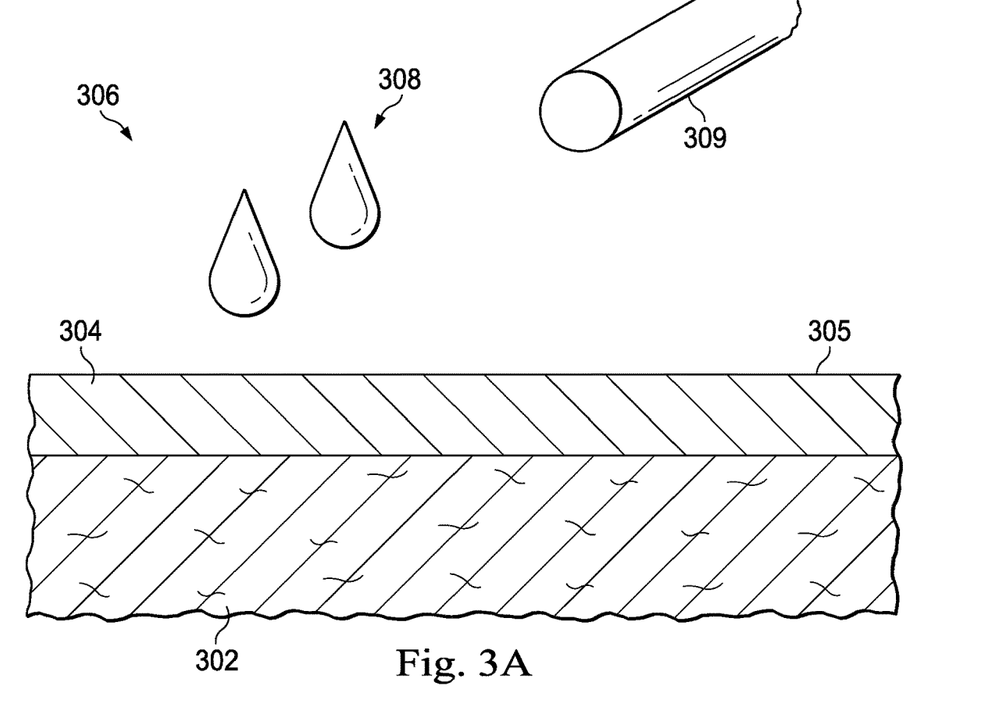
FIG. 3A is a diagram showing an illustrative inner limiting membrane in cross-section before a stain is applied.
Figure 3B:
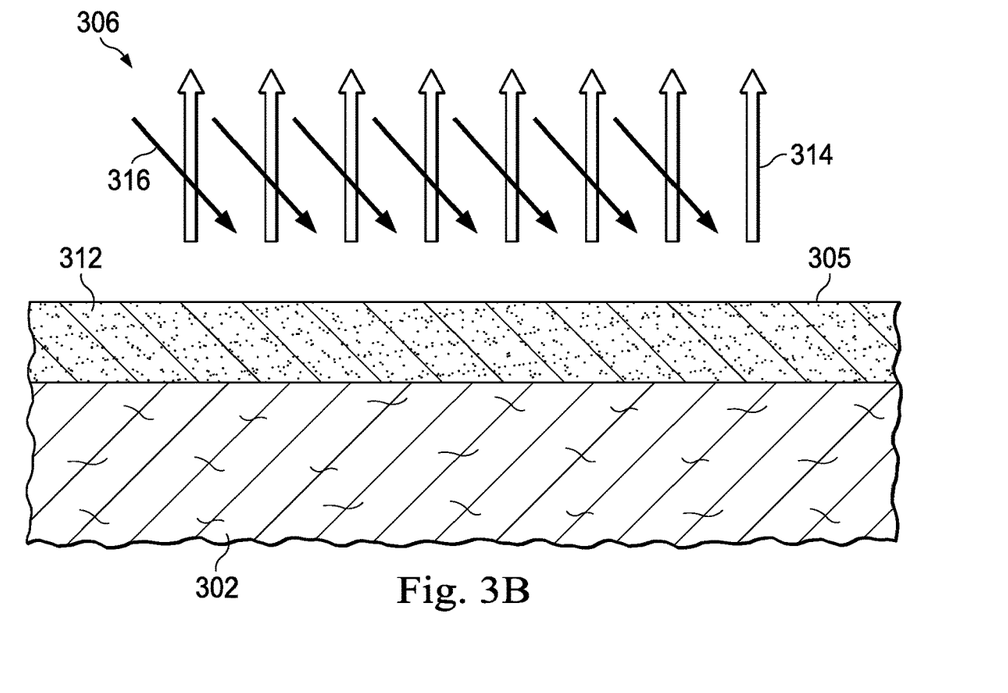
FIG. 3B is a diagram showing the illustrative inner limiting membrane of FIG. 3A in cross-section after stain is applied.

FIGS. 3A and 3B are illustrations used to visualize and explain a part of a process for staining and imaging ILM tissue. While the description herein is directed to staining and imaging an ILM 304 in order to treat an ocular condition of a patient, the systems and process described herein may be used to treat other types of tissue in other body regions or organs of a patient. FIG. 3A is a diagram showing an illustrative inner limiting membrane 304 before a stain 308 is applied. FIG. 3B is a diagram showing the stained ILM 312 when being subjected to excitation light 316. This allows an OCT imaging system to obtain better cross-sectional images below the surface 305 of the ILM 304.

Referring first to FIG. 3A, the ILM 304 separates the retina 302 from the vitreous 306. The retina 302 is the light sensitive portion of the eye. The vitreous 306 is a clear gel that fills the space between the retina 302 and the lens within the center of the globe of an eye. The ILM 304 itself is generally a transparent, colorless tissue layer. It is typically less than three micrometers thick, although in some instances, it may have a greater thickness. Thus, the ILM 304 is typically not easily resolvable using OCT imaging technologies.

According to principles described herein, a near-infrared fluorescent stain 308 is applied to the ILM 304. In some implementations, the stain 308 is a fluid and may be applied to the ILM 304 by penetrating the eye with a needle. The needle may be used to inject the stain 308 into the vitreous 306. The ILM 304 absorbs the stain 308 introduced into the vitreous 306. The near-infrared fluorescent stain 308 has various properties that cause it to produce fluorescent light having a wavelength within the near-infrared range when excited, such as by excitation light 316 shown in FIG. 3B.

FIG. 3B is a diagram showing an illustrative stained ILM 312. The stained ILM 312 is shaded to represent the ILM 304 of FIG. 3A after the stain 308 has been absorbed therein. With the stain 308 applied, an excitation light 316 is directed at the stained ILM 312. The excitation light 316 excites the stain 308 within the stained ILM 312 and causes the stain 308 to produce fluorescent light 314 having a wavelength within the near-infrared range. Different types of stains and different types of excitation light 316 may produce fluorescent light 314 with various ranges of wavelengths. In one example, the fluorescent light 314 may have a wavelength within a range of 700 nanometers to 1400 nanometers. In another example, the fluorescent light 314 may have a wavelength within a range of 750 nanometers to 1400 nanometers. In some examples, the fluorescent light 314 may have a wavelength greater than 700 nanometers. In some examples, the fluorescent light 314 may have a wavelength within a broader range that includes wavelengths within the visible spectrum. In some examples, the fluorescent light 314 may include light having a wavelength that is outside the visible spectrum. In some implementations, the fluorescent light 314 may have other wavelengths either larger or smaller than those mentioned above.

Figure 4:
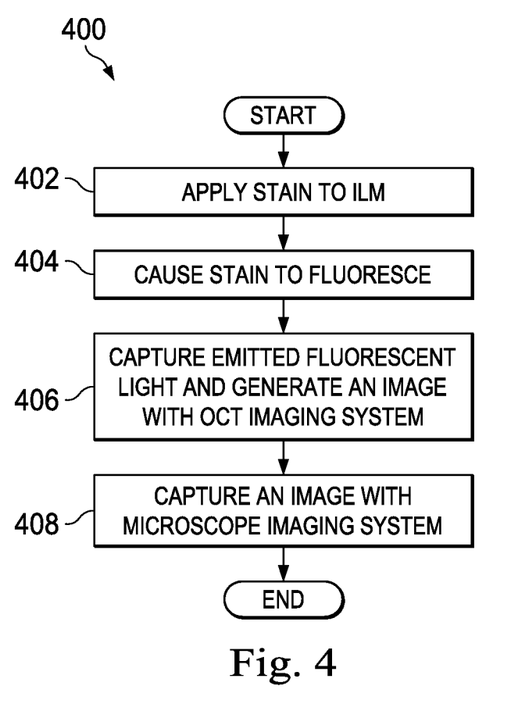
FIG. 4 is an example flowchart showing an illustrative method of using stain to visualize an inner limiting membrane.

FIG. 4 is a flowchart showing an illustrative method for using stain to visualize an ILM. According the present example, the method 400 includes a step 402 of applying a stain to the ILM. As mentioned above, some implementations of applying the stain may include injecting the stain into the vitreous of the eye. Injecting the stain may include introducing a stain injecting instrument, such as injecting instrument 309, into the globe of the eye. In some implementations, the stain injecting instrument may be a needle. The stain may be expelled from a distal end of the stain injecting instrument and into the posterior segment of the eye near the ILM. The stain then becomes absorbed by the ILM. Other implementations apply the stain in other ways. For example, in some implementations, the stain may be sprayed onto the ILM. In some instances, all or a portion of the vitreous may be removed prior to injecting the stain.

The method 400 further includes a step 404 of causing the absorbed stain to fluoresce. In the example implementation above, the stain may be caused to fluoresce by directing excitation light at the stained ILM. Fluorescent light produced by the stain in response to the excitation light may be within the near-infrared spectrum. In other words, when exposed to the excitation light within a desired wavelength range, the stain absorbed within the ILM will emit fluorescent light having a wavelength within the near-infrared range.

At step 406, the OCT imaging system captures the emitted fluorescent light and generates an image with the OCT imaging system. As described above, the OCT imaging system typically can capture light having a wavelength within the near-infrared range to generate images of tissue beneath the ILM surface. In some implementations, the OCT imaging system generates a cross-sectional view of the region of interest, and communicates the image to the image viewer 104. Such a view may be useful when performing any of a variety of ocular treatment procedures, including an ILM removal. Because the ILM has been stained, the image of the ILM generated by the OCT imaging system may be easier to see for a user. For example, the image may have increased contrast for tissue analysis or assessment during a surgical procedure. It may provide additional detail unseen without the stain. It may permit the user to more easily identify the boundaries of tissue and its location relative to the retina. These and other types of information may be considered by the user and may permit the user to perform treatment procedures and obtain better patient outcomes. Using principles described herein, the ILM is more visible within the OCT image. In some implementations, the OCT imaging system may capture real-time images, such as real-time video images, of a region of interest to provide to the user during an operation. In other implementations, the OCT imaging system may capture still-shots of the region of interest.

At step 408, the microscope imaging system captures an image. In the example implementation described herein, the microscope imaging system utilizes sensors that are sensitive to light having a wavelength within the near-infrared range. The captured image is communicated to the image viewer 104 and presented to the user. In some implementations, such as the example in FIG. 2, the OCT imaging system and the microscope imaging system both simultaneously provide images to the image viewer. These may be simultaneously displayed to the user. Thus, the user can be provided with a view of the ILM within the microscope image as well as the OCT image. The microscope imaging system may also capture images in real-time. Thus, the user can be provided with real-time images of the region of interest during an operation. The microscope imaging system may also capture still images. By providing both images to a user, and permitting a user to better visualize the OCT image of tissue using a stain as described herein, the user may be able to receive and process more information about the tissue, thereby enabling the user to make better decisions and have more successful treatment procedures.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method for imaging an inner limiting membrane of an eye, the method comprising:
    introducing a stain injecting instrument into the eye;
    applying a stain with the stain injecting instrument to vitreous of the eye such that the stain is absorbed by the inner limiting membrane of the eye;
    causing the stain to produce fluorescent light having a wavelength within a near-infrared range; and
    capturing the fluorescent light with an Optical Coherence Tomography (OCT) imaging system that is configured to detect light within the near-infrared range and producing an OCT image of the inner limiting membrane, epi-retinal membrane, or posterior vitreous cortex.

2. The method of claim 1, further comprising, capturing a microscope image of the inner limiting membrane, the epi-retinal membrane, or posterior vitreous cortex with a microscope imaging system.

3. The method of claim 2, wherein the microscope image and the OCT image are captured simultaneously.

4. The method of claim 2, wherein the microscope imaging system comprises a charge-coupled device (CCD) sensor that is sensitive to light within the near-infrared range.

5. The method of claim 2, wherein the microscope imaging system comprises a Complementary Metal-Oxide-Semiconductor (CMOS) sensor that is sensitive to light within the near-infrared range.

6. The method of claim 1, wherein causing the stain to produce the fluorescent light comprises directing an excitation light source at the stain.

7. The method of claim 6, wherein the excitation light source produces light having a wavelength within a range outside the near-infrared range.

8. The method of claim 1, wherein the OCT image includes a cross-sectional image below a surface of the inner limiting membrane, epi-retinal membrane, or posterior vitreous cortex.

9. A method comprising:
    introducing a stain injecting instrument into the eye;
    applying a stain with the stain injecting instrument to vitreous of the eye such that the stain is absorbed by an inner limiting membrane, epi-retinal membrane, or posterior vitreous cortex of an eye;
    directing light from an excitation light source at the stain to cause the stain to produce fluorescent light having a wavelength within a near-infrared range;
    capturing the fluorescent light with an Optical Coherence Tomography (OCT) imaging system and generating an OCT image of the inner limiting membrane, epi-retinal membrane, or posterior vitreous cortex with an OCT imaging system, the OCT imaging system configured to detect light within the near-infrared range; and
    while capturing the fluorescent light and generating the OCT image, capturing a microscope image of the inner limiting membrane, epi-retinal membrane, or posterior vitreous cortex with a microscope imaging system that is sensitive to light within the near-infrared range.

10. The method of claim 9, further comprising, simultaneously displaying the OCT image and the microscope image to a user.

11. The method of claim 9, wherein the near-infrared range is greater than 700 nanometers.

12. The method of claim 1 further comprising providing an image of the microscope image to an image viewer of a microscope.

* * * * *